United States Patent [19]

Marsella

[11] Patent Number: 4,745,190
[45] Date of Patent: * May 17, 1988

[54] SELECTIVE SYNTHESIS OF SUBSTITUTED AMINES

[75] Inventor: John A. Marsella, Allentown, Pa.

[73] Assignee: Air Products and Chemicals, Inc., Allentown, Pa.

[*] Notice: The portion of the term of this patent subsequent to Jul. 14, 2004 has been disclaimed.

[21] Appl. No.: 846,375

[22] Filed: Mar. 31, 1986

Related U.S. Application Data

[63] Continuation-in-part of Ser. No. 634,503, Jul. 25, 1984, abandoned.

[51] Int. Cl.$^4$ ................ C07D 265/30; C07D 207/00; C07C 85/06
[52] U.S. Cl. ..................... 544/170; 544/78; 548/524; 548/574; 564/479; 564/480
[58] Field of Search ............... 564/479, 480; 544/78, 544/170; 548/524, 574

[56] References Cited

U.S. PATENT DOCUMENTS

| | | | |
|---|---|---|---|
| 3,270,059 | 8/1966 | Winderl et al. | 260/583 |
| 3,708,539 | 1/1973 | Fenton | 260/585 B |
| 4,487,967 | 12/1984 | Stogryn et al. | 564/474 |

FOREIGN PATENT DOCUMENTS 0034480  8/1981  European Pat. Off. ............ 85/6

OTHER PUBLICATIONS

Brigg et al., J.C.S. Chem. Comm., pp. 611–612, (1981).
Murahashi et al., Tetrahedron Letters, (vol. 23, No. 2), pp. 229–232, (1982).
Arcelli et al., Journal of Organmetallic Chemisty, (vol. 235), pp. 93–96, (1982).

Primary Examiner—Charles F. Warren
Assistant Examiner—Elizabeth A. Hanley
Attorney, Agent, or Firm—Mark L. Rodgers; William F. Marsh; James C. Simmons

[57] ABSTRACT

Selective mono- or di-amination of alkanediols is controllably obtained by catalytic reaction with secondary amines at moderate temperature and autogenous pressure, by selection of the catalyst employed. Ruthenium complexes compounded or admixed with selected organic phosphines, such as triphenylphosphine, favor high yields of alkanolamines, while ruthenium complexes in the absence of organic phosphines favor production of alkylenediamines. Iridium complexes with or without organic phosphines in admixture or chemical combination, also promote production of alkylenediamines.

19 Claims, No Drawings

SELECTIVE SYNTHESIS OF SUBSTITUTED AMINES

CROSS REFERENCE TO PARENT APPLICATION

This is a continuation-in-part of U.S. patent application Ser. No. 634,503, filed July 25, 1984, now abandoned, the subject matter which is hereby incorporated by reference.

TECHNICAL FIELD OF THE INVENTION

The present invention relates to catalytic reactions of alkanediols with secondary amines and is particularly concerned with the controlled selective production of reaction products therefrom predominating respectively in (1) alkanolamines or (2) alkylenediamines.

BACKGROUND OF THE INVENTION

It is known to produce certain N-substituted alkanediamines and various alkanolamines from dichloroalkanes and alkylene oxides, respectively. These starting materials are expensive and/or extremely toxic. The toxic nature of some of the alkylene oxides is a special problem for small-scale users, since the unit costs of installing safe-guards and monitoring systems increase with decreasing production scale.

Previous prior art attempts at aminating alkanediols have been limited to high temperature reactions utilizing heterogeneous catalysts. The high temperatures required in the prior art methods led to high operating pressures and low selectivities.

A limited number of prior art disclosures describe the use of homogeneous catalysts, e.g. $RhH(PPh_3)_4$, for the reaction of monoalcohols with amines. (See, for example, Grigg, et al, *J. C. S. Chem. Comm.*, pp 611–612 [1981]).

European Patent Publication No. 034,480 describes in general the preparation of N-alkylamine or N,N-dialkylamine by reacting a primary or secondary amine with a primary or secondary alcohol in the presence of certain noble mtal catalysts, such as the metal, salt or complex of the noble metal. The preferred example of catalyst is a rhodium hydride-triphenylphosphine complex. Although the disclosure is concerned largely with reactions involving monofunctional alcohols, there is also disclosed the reaction of a primary amine with a diol for the formation of heterocyclic ring compounds containing the amine N atom. For this purpose, the diol used should contain at least four atoms in the chain so that cyclization can occur. The publication contains no disclosure of reaction of a diol with secondary amine, wherein cyclization is not possible.

An article by Murahashi, et al. in *Tetrahedron Letters* (vol. 23, No. 2, pp. 229–232, [1982]) describes the synthesis of secondary amines by reaction of alcohols with amines in the presence of $RuH_2(PPh_3)_4$ catalyst. By the reaction of butane diol or higher alkane diols with n-hexylamine, N-heterocyclic compounds are formed.

U.S. Pat. No. 3,708,539 discloses the condensation of amines with alcohols in the presence of ruthenium or certain other noble metal catalysts introduced as halides. The process is preferably conducted in the presence of a biphilic ligand of the structure $ER_3$, wherein E may be phosphorus or arsenic. Particular examples are directed to (1) reaction of butanol with dibutylamine obtaining tributylamine; (2) using hexanol as reactant in the same manner resulted in the formation of dibutylhexylamine.

U.S. Pat. No. 4,487,967 discloses a process for selectively preparing severely sterically hindered secondary aminoether alcohols by reacting a primary amino compound with a polyalkenyl ether glycol in the presence of a hydrogenation catalyst at elevated temperatures and pressures.

Reaction of diols with ammonia or alkylamines to produce diaminoalkanes is disclosed in U.S. Pat. No. 3,270,059. The reaction is carried out in the presence of hydrogen at 150°–300° C. and at a pressure of at least 10 atmospheres, over a solid catalyst which contains at least one metal from the group consisting of cobalt and nickel. When secondary amines are employed as reactants, tertiary diamines are obtained. Reaction of ethylene glycol with diethylamine under the conditions of the patent yields chiefly tetraethylethylene diamine and a lesser amount of diethylethanolamine.

The selective conversion of primary amines to yield (I) N,N-dimethylalkyl- or (II) N,N-dialkylmethylamines by reaction with methanol in the presence of $RuCl_2(Ph_3P)_3$ catalyst, is disclosed in an article by Arcelli, et al. in the Journal of Organometallic Chemistry (vol. 235, pp. 93–96 [1982]). The selectivity towards the I or II type compound is controlled by choice of the amount of catalyst and the ratio of reactants.

SUMMARY OF THE INVENTION

In accordance with the present invention, tertiary alkanolamines and alkanediamines are selectively produced in high yield from alkanediols selected from the group consisting of ethylene glycol and 1,3 propanediol, by reaction with secondary amines in the presence of ruthenium or iridium complexes. Selectivity favoring production of alkanolamines (i.e., mono-amination) is achieved by the use of a complex of a ruthenium compound with selected phosphine ligands, such as triphenylphosphine or a mixture of the ruthenium compound with such ligands. Selectivity toward production of alkanediamines (di-amination) is achieved by the use of an iridium complex catalyst with or without a phosphine modifier, or of the ruthenium compound in the presence of select phosphine components or in the absence of such components.

DETAILED DESCRIPTION

In practice of the invention, a solution of a secondary amine and alkanediol, such as ethylene glycol or 1,3 propanediol, is stirred in the presence of the ruthenium or iridium catalyst for two to six hours. The temperature range is maintained between about 100° to 125° C., with lower temperatures giving lower reaction rates and higher temperatures tending to effect dehydrogenation and/or decarbonylation of the diol.

The secondary amines can be represented by the formula: $HNR_2$ in which $-NR_2$ is

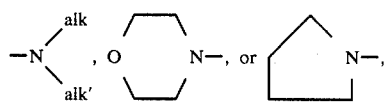

and in which "alk" and "alk'" are alkyl groups of up to 20 carbon atoms.

The alkanediols can include up to 12 carbon atoms with a linear or branched carbon skeleton. Preferably the hydroxyl functionalities should be separated by not more than one carbon. Examples of most preferred diols include ethylene glycol, and 1,3 propanediol.

The concentration of the secondary amine may be in the range of 0.5 to 10 mols per liter of reaction medium, and preferably 1 to 5 mols/liter. The catalyst concentration may be generally in the range of $10^{-4}$ to $10^{-1}$ moles per liter of reaction medium, and preferably $10^{-3}$ to $10^{-2}$ moles/liter.

Selectivity of the reaction can be altered to give mainly mono-amination (production of alkanolamines) or di-amination (production of alkylenediamines), by proper choice of catalyst. Proven catalysts that favor mono-amination are: $RuCl_2(PPh_3)_3$, $RuHCl(PPh_3)_3$; $RuCl_3.xH_2O$ admixed with about 3 moles/mole of $PPh_3$; $[Ru(NH_3)_6]Cl_3$ admixed with 3 moles/mole of $PPh_3$; $K_2[(RuCl_5)_2O]$, $Ru(NO)Cl_3$, $K_2RuCl_5$, $K_2RuCl_6$, and $[Ru(NH_3)_6]Cl_2$, each admixed with about 3 moles/mole of $PPh_3$. Also found to favor mono-amination was $K_2RuO_4$ admixed with about 5 moles/mole $PPh_3$. For these ruthenium-based systems, the selectivity preference progresses smoothly from mono- to di-amination as the amount of $PPh_3$ is decreased. In addition to the above listed ruthenium complexes other catalysts which are expected to favor mono-amination include: $K_2RuCl_6$, $K_2RuCl_5$, $RuCl_2(DMSO)_4$, "Ruthenium Red" (ammoniated ruthenium oxychloride), anhydrous $RuCl_3$, etc., each in admixture or molecular association with triphenylphosphine.

In general, based on observations, it can be stated that triarylphosphines substituted in the para position behave quite similarly to unsubstituted triphenylphosphine in admixture or in chemical combination with the listed ruthenium catalytic compounds. Those with ortho substituents show decreased rates of reaction with the selectivity tending toward diamination. The situation is more complex in the case of mixed aryl-alkyl-phosphines, including the potentially chelating diphosphines, bis(diphenylphosphino)methane (DPPM) and bis(diphenylphosphino)ethane (DPPE). Also included in this category are triphenylphosphite and tri-iso-propylphosphine. However, in most cases, it was observed that mono-amination is favored over di-amination by the addition of organic phosphine ligand as compared to the catalytic reaction in the absence of phosphine. As indicated by the listed examples, the organic phosphine compound may be initially introduced into the reaction medium as a separate component or in a form chemically combined with the platinum group metal catalyst, e.g. ruthenium or iridium. The organic phosphine compound or complex preferably is one corresponding to the formula:

$PR_1R_2R_3$ wherein $R_1$ and $R_2$ are each hydrogen or an alkyl or aryl hydrocarbyl group and $R_3$ is a hydrocarbyl group; each said hydrocarbyl group separately containing up to 12 carbon atoms.

Di-amination is selectively favored by $RuCl_3.xH_2O$ (phosphine-free), and by $IrCl_3.xH_2O$ (phosphine-free) or in admixture with triphenylphosphine, as well as by phosphine-free ruthenium mixtures and complexes such as: $K_2[(RuCl_5)_2O]$, $Ru(NO)Cl_3$, $K_2RuCl_5$, $K_2RuCl_6$, $RuCl_2(DMSO)_4$, and "Ruthenium Red", in the absence of mixed or chemically associated phosphines.

The catalysts employed in practice of the invention, without being bound to any particular theory, apparently function as homogeneous catalysts, since they are at least partially dissolved in the reaction medium. As a result, such catalysts obtain more selective product distribution than that obtained using heterogeneous catalysts. Moreover, catalyst modifiers, such as the triphenylphosphine in the instant case, have a marked effect on the activity of homogeneous catalysts. Thus, by the practice of the present invention, the selective manufacture of desired alkanolamines or of the desired di-amines is made possible utilizing readily available and relatively low toxicity starting materials. Furthermore, the desired products are readily obtained under relatively mild operating conditions, preferably at autogenous pressure, and temperatures in the range of about 100° to 125° C., without requiring addition of hydrogen to the system, although hydrogen may be employed, if desired.

The exact composition and structure of the active catalyst species promoting the reaction is not clear, since the form in which the catalyst is introduced may function merely as a precursor to the active structure formed in the medium under reaction conditions. While carbonyl complexes have been observed in reaction mixtures, the use of isolated neutral carbonyl complexes of ruthenium as such catalyst precursors were found to lead to lower catalytic activity.

Among other active catalysts favoring di-amination, good results are obtained with $IrH(Cl)_2(PPh_3)_3$. Iridium carbonyl complexes, like the ruthenium carbonyl complexes, show decreased overall activity. Surprisingly, however, $IrH_2Cl(PPh)_3$ showed relatively low overall activity, but favored di-amination.

The process of the invention may be carried out in the presence of added solvents or diluents, among which are preferred; N-methylpyrrolidinone, N,N-dimethylacetamide, dimethylsulfoxide (DMSO), water, 1,2-dimethoxyethane.

While on the basis of prior art disclosures, it was expected that ruthenium and rhodium-based catalysts would show similar behavior in the promotion of amination reactions, it was unexpectedly found in preliminary experiments that this was not the case in reactions of diols, particularly ethylene glycol and 1,3 propanediol, with secondary amines.

Several experimental runs were carried out in accordance with the present process. These runs are set out in the examples reported below. These examples are only meant to illustrate the present invention and are not meant to be limiting.

All of the runs, unless stated otherwise, were carried out under nitrogen atmosphere. The GC analyses were performed using a copper column with 15% Carbowax 20M on Gaschrom Q as the stationary phase. All reaction vessels were charged in a glove box under an inert ($N_2$) atmosphere.

The reactions at 120° C. were carried out in a 22 ml Parr stainless steel pressure vessel while the reactions at 100° and 110° C. with liquid sampling were carried out in a small flask equipped with a septum sealed side arm and fitted with a reflex condenser. Quantitation was by the internal standard method with 1-methyl-2-pyrrolidinone added as the reference. Liquid amines were added directly to the reaction vessel while gaseous amines were first dissolved in ethylene glycol or other diol to form a solution of known concentration, of which a known volume was charged to the reaction vessel.

EXAMPLE 1

A series of experimental runs were carried out with various diols and different secondary amines at a reaction temperature of 120°–125° C. for 2–2.5 hours. The amine concentration in each of the runs was about 1.8M and the catalyst concentration about $2\times10^{-2}$M. The reactants and catalysts employed in these runs are set out in Table 1, wherein the reactants are designated by: EG=ethylene glycol, PRDIOL=propanediol, MOR=morpholine, DMA=dimethylamine, DEA=diethylamine, DIPA=di-isopropylamine. Total selectivity (selec) is defined as $$\frac{Ym + Yd}{\text{Conversion}} \times 100\%, \text{ where } Ym = \text{yield}$$

of mono-aminated product(s) and Yd=yield of diaminated product(s).

The relative selectivities, mono- vs di-, is expressed as a selectivity coefficient (r) wherein:

$$r = \frac{Yd}{Ym + Yd}$$

TABLE 1

| Run No. | Amine | Diol | Catalyst | Conversion % | Total Selec % | r |
|---|---|---|---|---|---|---|
| 1 | MOR | EG | $RuCl_2(PPh_3)_3$ | 100 | 92 | 0.09 |
| 2 | DMA | EG | $RuCl_2(PPh_3)_3$ | 100 | 85 | 0.04 |
| 3 | DMA | 1,2 PRDIOL | $RuCl_2(PPh_3)_3$ | 67 | 95 | 0.06 |
| 4 | DMA | 1,3 PRDIOL | $RuCl_2(PPh_3)_3$ | 85 | 66 | 0.01 |
| 5 | DIPA | EG | $RuCl_2(PPh_3)_3$ | 20 | 100 | 0 |
| 6 | MOR | EG | $RuCl_3.xH_2O$ | 100 | 96 | 0.83 |
| 7 | DMA | EG | $RuCl_3.xH_2O$ | ca 90 | >90 | 0.89 |
| 8 | DMA | 1,2- PRDIOL | $RuCl_3.xH_2O$ | 41 | 81 | 0.39 |
| 9 | DMA | 1,3- PRDIOL | $RuCl_3.xH_2O$ | 70 | 51 | 0.88 |
| 10 | MOR | EG | $IrCl_3 + 3PPh_3$ | 79 | 90 | 0.89 |
| 11 | DMA | EG | $IrCl_3 + 3PPh_3$ | 76 | 72 | 0.87 |
| 12 | DMA | 1,2- PRDIOL | $IrCl_3 + 3PPh_3$ | 36 | 66 | 0.36 |
| 13 | DMA | 1,3- PRDIOL | $IrCl_3 + 3PPh_3$ | 45 | 43 | 0.93 |
| 14 | DEA | EG | $RuCl_2(PPh_3)_3$ | 98 | 92 | 0.01 |
| 15 | DEA | EG | $RuCl_3.xH_2O$ | 42 | 98 | 0.85 |

EXAMPLE 2

Another series of runs was carried out under conditions of Example 1 to determine the effect of the triphenylphosphine to ruthenium ratio (P:Ru) on the reaction of ethylene glycol with morpholine, catalyzed by mixtures of $RuCl_3.xH_2O$ with $PPh_3$. The results are reported in Table 2.

TABLE 2

| Run | P:Ru | Conversion % | r | Total Selectivity % |
|---|---|---|---|---|
| 14 | 0 | 60 | .91 | 82 |
| 15 | 0 | 100 | .83 | 95 |
| 16 | 0 | 100 | .83 | 96 |
| 17 | 0.5 | 53 | .53 | 91 |
| 18 | 1.0 | 79 | .22 | 90 |
| 19 | 3.0 | 95 | .05 | 91 |

As seen from the above-tabulated results, by the judicious use of triphenylphosphine as catalyst modifier with ruthenium complexes, selectivity of the reaction can be altered to obtain high conversion to (i) mono-aminated or (ii) di-aminated products, as represented by the equations:

$$HOCH_2CH_2OH + HNR_2 \rightarrow HOCH_2CH_2NR_2 + H_2O \quad (i)$$

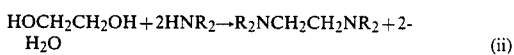

$$HOCH_2CH_2OH + 2HNR_2 \rightarrow R_2NCH_2CH_2NR_2 + 2H_2O \quad (ii)$$

in which —$NR_2$ is the same as that defined under the Detailed Description.

EXAMPLE 3

Another series of runs was carried out in the amination of ethylene glycol with various secondary amines in the presence of $RuCl_2(PPh_3)_3$ as the added catalyst at 120° C. These runs were made using 5 ml of glycol to 0.011–0.012 mol. amine and 1 mol% Ru (based on amine). The results are tabulated in Table 3.

TABLE 3

| Amine | pyrrolidine | morpholine | dimethylamine |
|---|---|---|---|
| Time (hr) | 6 | 2 | 3 |
| Conv. (%) | 100 | 100 | 100 |
| Selectivity (%) | | | |
| $R_2NCH_2CH_2OH$ | 79 | 83 | 81 |
| $R_2NCH_2CH_2NR_2$ | (observed) | 9 | 4 |

It will be seen from Table 3 that high conversion is obtained with the ruthenium catalyst at moderate temperature, and unexpectedly high selectivity to substituted ethanolamines.

Some increase in pressure was noted in the runs at 120° C., but these increases amounted to only about 15 psig (at 25° C.) in a 22 ml Parr vessel. In contrast, higher temperature runs led to net pressure increases of 60–70 psig. Thus, the lower temperature apparently prevents hydrogen loss from the reaction system—an observation consistent with higher sensitivity to the simple amination products at the lower temperatures.

EXAMPLE 4

The effect of varying the starting Ru complex on product distributions is shown in Table 4. These runs were made using ethylene glycol with morpholine as the secondary amine; 5 ml of glycol were used per gram of morpholine (=0.0115 mol) and 1 mol% Ru (based on morpholine).

TABLE 4

| Complex | $RuCl_2.(PPh_3)_3$ | $RuHCL.(PPh_3)_3$ | $RuCl_3.xH_2O + 3PPh_3$ | $RuCl_3.xH_2O$ |
|---|---|---|---|---|
| Time (hr) | 6 | 5.5 | 2 | 2 |
| Temp (°C.) | 100 | 100 | 120 | 120 |
| Conv (%) | 89 | 94 | 95 | 100 |
| Selec (%): | | | | |
| $R_2NCH_2CH_2OH$ | 94 | 90 | 88 | 15 |
| $R_2NCH_2CH_2NR_2$ | 3 | 2 | 2 | 80 |

EXAMPLE 5

While in the previous examples the secondary amine employed was free of other functional groups, the invention is also applicable to functionally substituted secondary amines.

The procedure described in Example 3 was employed using N,N,N'-trimethylethylenediamine as the secondary amine. The reaction product was analyzed by gas-liquid chromatography and was found that 2-[[2-(dimethylamino)ethyl]methylamino]ethanol had been formed in 91% yield, in a 2.5 hour operation.

EXAMPLE 6

While the reactions in accordance with the invention do not require the presence of added hydrogen, it may be desired in some instances to carry out the process in the presence of hydrogen.

The procedure described in Example 3 was employed in the amination of ethylene glycol with morpholine as the secondary amine. The reaction vessel was charged with hydrogen (at 25° C.) to a pressure of 50 psig (=4.55 Kg/cm$^2$). After heating the contents of the reactor at 125° C. for 2.5 hours, the vessel was cooled and vented. Analysis by gas-liquid chromatography showed 60% conversion of the morpholine to N-2-(hydroxyethyl)morpholine (63% selectivity) and 1,2-bis(-morpholino)ethane (30% selectivity). From the foregoing run it will be seen that the presence of hydrogen leads to a retardation of the reaction rate as well as to alteration of reaction selectivity. Thus, the ratio in this instance was r=0.32, as compared to r=0.09 in Run No. 1 of Table 1.

A number of runs were carried out to determine the effect of various phosphine additives on RuCl$_3$.xH$_2$O catalyzed reactions of morpholine with ethylene glycol. The conditions employed were substantially the same as used in Example 1, unless otherwise indicated. The results are reported in Table 5.

TABLE 5

| L | L:Ru | Temp (°C.) | Time hrs. | Conv. (%) | Total Selec (%) | r |
|---|---|---|---|---|---|---|
| P(p-C$_6$H$_4$F)$_3$ | 3.0 | 120 | 2.5 | 100 | 95 | <0.01 |
| P(Ph)Me$_2$ | 3.0 | 125 | 2.5 | 100 | 88 | 0.08 |
| P(p-tol)$_3$ | 2.9 | 128 | 2.25 | 100 | 93 | 0.17 |
| P(C$_6$F$_5$)$_3$ | 2.5 | 120 | 3 | 22 | 60 | >0.6 |
| P(OPh)$_3$ | 3.2 | 125 | 2.5 | 13 | 48 | 0.69 |
| DPPM | 1 | 120 | 2 | 70 | 91 | 0.73 |
| PPh$_2$Me | 3.0 | 125 | 2.5 | 45 | 88 | 0.73 |
| P(i-Pr)$_3$ | 3.8 | 120 | 2.5 | 12 | 44 | 0.75 |
| DPPE | 1 | 125 | 2 | 13 | 57 | 0.82 |
| PPh(C$_6$F$_5$)$_2$ | 3.6 | 117 | 3 | 100 | 84 | 0.84 |
| P(o-C$_6$H$_4$NMe$_2$) | 2.7 | 120 | 2 | 37 | 90 | 0.94 |
| P(o-tol)$_3$ | 2.9 | 130 | 2.5 | 48 | 85 | 0.95 |

Me = methyl; Ph = phenyl; tol = tolyl;
DPPM = bis (diphenylphosphino)methane
DPPE = bis (diphenylphosphino)ethane.

Other runs made under the reported conditions gave the results shown in Table 6.

TABLE 6

| Catalyst | % Conv. | r | % Total Selectivity |
|---|---|---|---|
| [(MePh$_2$P)$_3$Ru($\mu$-Cl)$_3$Ru(MePh$_2$P)$_3$] | 100 | 0.63 | 97 |
| [(Me$_2$PhP)$_3$Ru($\mu$-Cl)$_3$Ru(Me$_2$PhP)$_3$] | 100 | 0.15 | 89 |

EXAMPLE 7

To determine the effect of added phosphine compound to iridium catalyst, a run was carried out using IrCl$_3$.xH$_2$O in the absence of phosphine or other catalyst modifier, under conditions employed in Example 1 above. In the reaction of morpholine with ethylene glycol at 20% conversion of the morpholine, hydroxylethylmorpholine was obtained at 10% selectivity and 1,2-bis(morpholino)ethane at 56% selectivity. The results obtained in the same reaction with 3 moles PPh$_3$ added per mole of IrCl$_3$ is reported in Table 1, Run No. 10. In the presence of PPh$_3$, higher overall conversion is obtained with the iridium catalyst and considerably higher selectivity (90%) to di-amination.

While in the illustrative operating examples (at temperatures ranging from 100°–125° C.) employing phosphine as a catalyst modifier, the ratio of P:Ru is up to about 3:1, the invention is not limited thereto. Good results have been obtained at P:Ru ratios up to 5:1, and while, at this temperature range, no special benefits are known to be obtained thereby, higher P:Ru ratios as up to about 10:1 may be employed.

EXAMPLE 8 (Comparative)

A comparative run was carried out in accordance with the general procedures set out for examples 1–7 above using the catalyst system and mono-alcohol disclosed in the Arcelli article cited above. Morpholine was reacted with methanol in the presence of RuCl$_2$(PPh$_3$)$_3$ as a catalyst. The reaction was carried out at a temperature of 120° C. for about 2½ hours.

The resulting product was a clear, very dark red solution. Subsequent GC analysis indicated that there was only about an 8.4% conversion of morpholine.

The results of this run indicate that, at the temperature range of the present invention, amination of a mono-alcohol with a secondary amine using the present catalyst system, results in a very low product yield.

EXAMPLE 9 (Comparative)

A comparative run was carried out in accordance with the general procedures set out in the above examples. In this example diethylamine, a secondary amine which was specifically recited in U.S. Pat. No. 3,270,059, was reacted with methanol in the presence of RuCl$_2$(PPh$_3$)$_3$ at a temperature of 120° C.

The reaction was allowed to proceed for about 2½ hours, after which a clear, amber supernatant solution was collected and a GC analysis was performed. The results of the GC analysis indicated that there was a 25.3% conversion with only an 8.2% aminated product yield.

Examples 8 and 9 above indicate that, within the temperature range of the present invention (100°–125° C.), the present catalyst system does not produce a high yield of amination products when using a secondary amine and a mono-alcohol. Conversely, it has been found that only amination reactions using diols and secondary amines with the present catalyst system produce significant yields of the desired products at a temperature range between 100°–125° C.

EXAMPLE 10 (Comparative)

A run was carried out reacting morpholine with ethylene glycol using the same catalyst and under the same conditions as Example 1 above, except the reaction temperature was maintained at about 180° C. The reaction product was analyzed as described above, and an essentially 1:1 distribution between mono- and di-aminated product was found.

This data indicate that the high temperatures disclosed in Arcelli needed to promote good yields in the reaction of methanol with primary amines, does not result in the desired product selectivity for reactions of diols with secondary amines.

EXAMPLE 11 (Comparative)

Under the same conditions (120°–125° C.) reported in Example 1 (above) a run was carried out using as catalyst $RhCl_3.3H_2O$ (43% Rh) admixed with 3 moles $PPh_3$ per mole Rh, in the amination of ethylene glycol by reaction with morpholine. The overall conversion to aminated products was 27% with 23% selectivity in the production of hydroxyethylmorpholine and 42% selectivity in the production of bix(morpholino)ethane.

This example indicates that rhodium complexes have some activity under these conditions, but are generally inferior to ruthenium. Additionally, the rhodium catalyst did not exhibit the product selectivity; mono- vs. di-amination, that was achieved with the ruthenium.

Having thus described the present invention, what is now deemed appropriate for Letters Patent is set out in the following appended claims.

What is claimed:

1. In the catalytic amination of ethylene glycol or 1,3 propanediol with a secondary amine, the method for selectively favoring the formation of mono-aminated products which comprises:
    effecting said amination at a temperature in the range of 100° to 125° C. in the presence of a catalyst consisting of a compound or complex of ruthenium in chemical combination or in admixture with an organic phosphine modifier selected from the group consisting of $PPh_3$, $P(p-C_6H_4F)_3$, $P(Ph)Me_2$, $P(p-tol)_3$ and mixtures thereof, in an amount to provide at least one mole of organic phosphine per gram atom of ruthenium.

2. The method in accordance with claim 1 wherein said catalyst is at least partially dissolved in a liquid reaction medium.

3. The method in accordance with claim 1 wherein said catalyst is selected from the group consisting of:
    (1) $RuCl_2(PPh_3)_3$, $RuHCl(PPh_3)_3$; and
    (2) the following compounds in admixture with $PPh_3$: $Ru(NH_3)_6Cl_3$, $K_2(RuCl_5)_2O$, $Ru(NO)Cl_3$, $K_2RuCl_5$, $K_2RuCl_6$, $Ru((NH_3)_6Cl_2$ and $K_2RuO_4$.

4. The method in accordance with claim 1 wherein said catalyst is a compound selected from the group consisting of:
    $Ru(NH_3)_6Cl_3$, $K_2(RuCl_5)_2O$, $Ru(NO)Cl_3$, $K_2RuCl_5$, $K_2RuCl_6$, and $Ru(NH_3)_6Cl_2$, each admixed with about 3 moles of triphenylphosphine per gram atom of ruthenium.

5. The method as defined in claim 1 wherein said amination is effected at a temperature in the range of 120° to 125° C.

6. The method as defined in claim 1 wherein said amination is effected in the absence of added hydrogen and at autogeneous pressure.

7. The method as defined in claim 1 wherein said secondary amine is selected from the group consisting of: morpholine, dimethylamine, diethylamine, di-isopropylamine, N,N,N'-trimethylethylene diamine and pyrrolidine.

8. The method as defined in claim 1 wherein said amination is carried out in the liquid phase.

9. The method as defined in claim 1 wherein said amination is carried out with the secondary amine dissolved in the diol at an amine concentration of about 1.8 molar and at a dissolved catalyst concentration of about one-hundredth that of the amine.

10. In the catalytic amination of ethylene glycol or 1,3 propanediol with a secondary amine, the method for selectively favoring the formation of di-aminated products which comprises: effecting said amination at a temperature in the range of 100° to 125° C. in the pressure of a catalyst selected from the group consisting of (1) a ruthenium compound or complex in the absence of an organic phosphine modifier, (2) a ruthenium compound or complex in admixture or chemical combination with an organic phosphine modifier selected from the group consisting of $PPh(C_6F_5)_2$, $P(o-C_6H_4NMe_2)$, $P(o-tol)_3$ and mixtures thereof, and (3) an iridium compound or complex free of modifier or in chemical combination or admixture with an organic phosphine modifier; said catalyst modifier being present in an amount sufficient to provide at least one mole or organic phosphine per gram atom of ruthenium.

11. The method in accordance with claim 10 wherein said catalyst is at least partially dissolved in a liquid reaction medium.

12. The method in accordance with claim 10 wherein said catalyst is selected from the group consisting of phosphine free $RuCl_3.xH_2O$ and $IrCl_3.xH_2O$.

13. The method in accordance with claim 10 wherein said catalyst is $IrCl_3.xH_2O$ in chemical combination or in admixture with triphenyl phosphine.

14. The method in accordance with claim 10 wherein said amination is effected at a temperature in the range of 120° to 125° C.

15. The method in accordance with claim 10 wherein said amination is effected in the absence of added hydrogen and at autogenous pressure.

16. The method as defined in claim 10 wherein said secondary amine is selected from the group consisting of: morpholine, dimethylamine, diethylamine, di-isopropylamine, N,N,N'-trimethylethylene diamine and pyrrolidine.

17. The method as defined in claim 10 wherein said amination is carried out in the liquid phase.

18. The method as defined in claim 10 wherein said amination is carried out with the secondary amine dissolved in the diol at an amine concentration of about 1.8 molar and at a dissolved catalyst concentration of about one-hundredth that of the amine.

19. In the catalytic amination of an alkanediol selected from the group consisting of ethylene glycol and 1,3 propanediol, with a secondary amine, the method of selectively controlling the relative extent of
    (A) mono-amination and (B) di-amination of said diol which comprises: effecting said amination at a temperature in the range of 100° to 125° C. in the presence of a catalyst comprising a ruthenium or iridium complex at least partially dissolved in liquid reaction medium, wherein said catalyst is provided by the introduction of (a) a compound or complex of ruthenium in chemical combination or admixture with an organic phosphine catalyst modifier selected from the group consisting of $PPh_3$, $P(p-C_6H_4F)_3$, $P(Ph)Me_2$, $P(p-tol)_3$ and mixtures thereof, in an amount to provide at least one mole of organic phosphine per gram atom of ruthenium to selectively favor mono-amination; or as (b) a catalyst selected from the group consisting (1) a ruthenium compound or complex in the absence of an organic phosphine modifier, (2) an iridium compound or complex free of modifier or in admixture or chemical combination with an organic phosphine modifier, and (3) a ruthenium compound in admixture or chemical combination with an organic phosphine catalyst modifier selected from the group consisting of $PPh(C_6F_5)_2$, $P(o-C_6H_4MNe_2)_3$, $P(o-tol)_3$ and mixtures thereof, to selectively favor di-amination.

* * * * *